United States Patent
Prasitchoke et al.

(10) Patent No.: US 12,018,245 B2
(45) Date of Patent: Jun. 25, 2024

(54) YEAST HAVING IMPROVEMENT OF LACTIC ACID TOLERANCE AND USE THEREOF

(71) Applicant: PTT Global Chemical Public Company Limited, Bangkok (TH)

(72) Inventors: Phatthanon Prasitchoke, Bangkok (TH); Natthawut Poomsila, Bangkok (TH); Kraileark Kittisuriyanont, Bangkok (TH); Narong Kaewsuwan, Bangkok (TH); Wikanda Techanan, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 0 days.

(21) Appl. No.: 17/634,876

(22) PCT Filed: Aug. 19, 2019

(86) PCT No.: PCT/TH2019/000030
§ 371 (c)(1),
(2) Date: Feb. 11, 2022

(87) PCT Pub. No.: WO2021/034276
PCT Pub. Date: Feb. 25, 2021

(65) Prior Publication Data
US 2022/0411745 A1 Dec. 29, 2022

(51) Int. Cl.
*C12N 1/16* (2006.01)
*A61K 36/064* (2006.01)

(52) U.S. Cl.
CPC ............ *C12N 1/165* (2021.05); *A61K 36/064* (2013.01)

(58) Field of Classification Search
None
See application file for complete search history.

(56) References Cited

U.S. PATENT DOCUMENTS 9,085,781 B2   7/2015  Zahn et al.
9,758,564 B2   9/2017  Lee et al.
(Continued)

FOREIGN PATENT DOCUMENTS

WO   WO-2015194900 A1 * 12/2015 ........... C12N 15/815
WO   2016083397 A1   6/2016

OTHER PUBLICATIONS

Kurtzman, Cletus P; "Phylogenetic circumscription of *Saccharomyces*, Kluyveromyces and other members of the Saccharomycesceae, and the proposal of the new genera Lachancea, Nakaseomyces, Naumovia, Vanderwaltozyma and Zygotorulaspora" FEMS Yeast Research, 4, 233-245, 2003 (Year: 2003).*

(Continued)

*Primary Examiner* — David W Berke-Schlessel
(74) *Attorney, Agent, or Firm* — TROUTMAN PEPPER HAMILTON SANDERS LLP

(57) ABSTRACT

The present invention discloses a genetically engineered *Kluyveromyces* sp. yeast cell comprising at least a genetic modification that inactivates or deletes a nucleotide sequence encoding for transcription factor SEQ ID No. 2, particularly Haa1. The genetically engineered yeast cell according to this invention has an improvement of lactic acid tolerance, lactic acid production or a combination thereof as compared to the parental.

4 Claims, 6 Drawing Sheets

Specification includes a Sequence Listing.

(56) References Cited

U.S. PATENT DOCUMENTS 9,994,877 B2    6/2018   Chung et al.
10,053,714 B2   8/2018   Chu et al.

OTHER PUBLICATIONS

Rugthaworn, Prapassorn; et al.; "Growth Inhibition of Thermotolerant Yeast, Kluyveromyces marxianus, in Hydrolysates from Cassava Pulp" Applied Biochemistry and Biotechnology, 173, 1197-1208, 2014 (Year: 2014).*
Juergens et al. (2018) Genome editing in *Kluyveromyces* and *Ogataea* yeasts using a broad-host-range Cas9/gRNA co-expressionplasmid. FEMS Yeast Research, vol. 18, No. 3.
Tanaka et al. (2012) Enhancement of Acetic Acid Tolerance in *Saccharomyces cerevisiae* by Overexpression of the HAA1 Gene, Encoding a Transcriptional Activator. Applied and Environmental Microbiology, vol. 78, No. 22, pp. 8161-8163.
Suzuki et al. (2013) Disruption of multiple genes whose deletion causes lactic acid resistance improves lactic-acid resistance and productivity in Saccharomyces cerevisiae. Journal of Bioscience and Bioengineering, vol. 115, Issue 5, pp. 467-474.

* cited by examiner

YEAST HAVING IMPROVEMENT OF LACTIC ACID TOLERANCE AND USE THEREOF

This application is a U.S. national stage application of International Application No. PCT/TH2019/000030, filed on Aug. 19, 2019, the entire contents of which is hereby incorporated by reference in its entirety.

FIELD OF THE INVENTION

Biotechnology especially genetic engineering which relates to yeast having improvement of lactic acid tolerance and use thereof

BACKGROUND OF THE INVENTION

The organic acids that are produced from renewable resources are becoming attractive molecules for several industries. In the energy industry, the bioethanol and biobutanol have been long time developed and commercially used. Lactic acid and succinic acid which are also 0 biologically produced and used as raw materials in various applications e.g., food & feed additives in food industry, mild solvent applications in personal care production and bio-polymer synthesis for bio-based resin productions. All aforementioned molecules are produced by the well-known processes called fermentation. The most challenge of the fermentation process is the production cost.

Several attempts to reduce the production cost have been approached. To reduce the cost of fermentation feedstock, agricultural waste e.g., bagasse from sugar industry, have been proposed. Cellulose from bagasse can be physically and chemically broken down into fermentable sugar for bacteria utilization. However, various impurities from the pretreatment process cause the inhibition effect to bacteria. For instance, acetate released from the hemicellulose breakdown is the well-known inhibitor of most microorganism. Moreover, the undesired lactic acid from the contaminations of some bacteria during bagasse storage can also affect to the fermentation process.

On the other hand, the problems to prevent the cell damages during fermentation are also costly. For instance, it occurs in the case of weak acid, e.g., lactic acid and succinic acid productions. During the fermentation of these acids, it is important to neutralize the lactic acid produced and desalination of the resulting lactate to prevent the cell activities damage from lowing pH. Among the powerful bacteria using in the biotechnological process, yeast have been mostly used because of its robustness and low pH tolerance. Still, below pH values of 2.8, lactic acid production with the engineered yeast strain dropped. Therefore, conferring higher lactic 3 acid resistance on yeast would improve lactic acid productivity under non-neutralized conditions.

Several studies have been conducted in *Saccharomyces cerevisiae* yeast whereby it is clearly indicated that the yeast cell responds to acid by regulation of a transcription factor encoded by HAA1 gene.

Sugiyama et al. (Applied and Environmental Microbiology, 2014, 80, 3488-3495) approached to overexpress HAA1 gene encoding for the transcription factor, to mimic the relocalization of its protein, Haa1p into nuclease whereby they consequently induce the weak acid adaptation mechanisms in order to improve lactic acid resistance in *Saccharomyces cerevisiae*. This study also found that the haa1 disruptant caused severe lactic acid sensitivity compared to parental strain.

Tanaka et al. (Applied and Environmental Microbiology, 2012, 78, 8161-8163) disclosed similar results about the overexpression of HAA1 in *Saccharomyces cerevisiae* that could enhance the acetic acid tolerance.

U.S. Pat. No. 9,085,781B2 and Swinnen et al. (Microbial Cell Factories, 2017, 16:7, 1-15) attempted to induce point mutations to fine tune the HAA1 expression in *Saccharomyces cerevisiae*; therefore, it resulted in a higher acetic acid resistance as compared to the wild-type allele.

WO2016083397A1 disclosed the combination of HAA1 and its paralog CUP2 to achieve the improvement of acid tolerance in yeast, especially *Saccharomyces cerevisiae*. These complexities cause mainly the obstacles to use this approach in commercialized scale of production.

Furthermore, there have been some studies in this research area in yeast strains, especially *Saccharomyces cerevisiae*, so as to improve lactic acid tolerance but did not involve with HAA1 gene.

U.S. Pat. No. 9,994,877B2 disclosed a genetically engineered yeast cell increased the activity of SUL1, STR3, AAD10, MXR1, GRX8, MRK1, GRE1, HIX7, ERR1, or a combination thereof. The obtained yeast strain has increased acid tolerance as compared to its parent cell and is useful for producing lactate.

U.S. Pat. No. 9,758,564B2 disclosed an acid-resistant yeast cell with reduced the expression of a polynucleotide that encodes the Fps1 in order to increase the lactic acid resistance.

U.S. Ser. No. 10/053,714B2 disclosed an acid-tolerant genetically engineered yeast cell comprising 3 a genetic modification of increasing an activity of an enzyme that catalyzes conversion of phosphatidylinositol (PI) and ceramide to inositol phosphorylceramide (IPC) and diacylglycerol (DG) or increasing an activity of an enzyme which catalyzes introduction of a double bond to a fatty acyl site of a fatty acyl-CoA and/or decreasing an activity of an enzyme which catalyzes formation of triacylglycerol (TG) from DG or a combination thereof and optionally reducing activity of external mitochondrial NADH dehydrogenase NDE1 and/or NDE2 which could increase a tolerance of an organic acid having 1-20 carbon atoms especially lactic acid.

Suzuki et al. (Journal of Bioscience and Bioengineering, 2013, 115, 467-474) reported a construction of acid resistant yeast in *Saccharomyces cerevisiae* by combining gene disruptions that led to lactic-acid resistance. This study found that 94 gene disruptants showed resistance to lactic acid and that lactic-acid resistance was further enhanced by combining the disruption of several genes which leading to high lactic-acid productivity without neutralization.

From the reason mentioned above, this invention discloses the simple approach to enhance lactic acid tolerance in the other non-conventional yeast, particularly *Kluyveromyces sp.*, in which the deletion of HAA1 is sufficiently cause the improvement of its lactic acid tolerance, lactic acid production or a combination thereof.

The improved yeast from the present invention can be used in broad aspects, for example but not limit to, fermentation process by using low-cost feedstock that containing any acid impurities and perform the fermentation to produce a fermentation broth with high levels of free lactic acid. Those advantages are the cost-effectiveness production.

SUMMARY OF THE INVENTION

The present invention relates to a genetically engineered *Kluyveromyces sp.* yeast cell comprising at least a genetic modification that inactivates or deletes a nucleotide sequence encoding for an amino acid SEQ ID No. 2, particularly Haa1.

The genetically engineered yeast cell according to this invention has an improvement of lactic acid tolerance, lactic acid production or a combination thereof as compared to the parental.

DETAILED DESCRIPTION OF THE INVENTION

Definition

Figure 1:
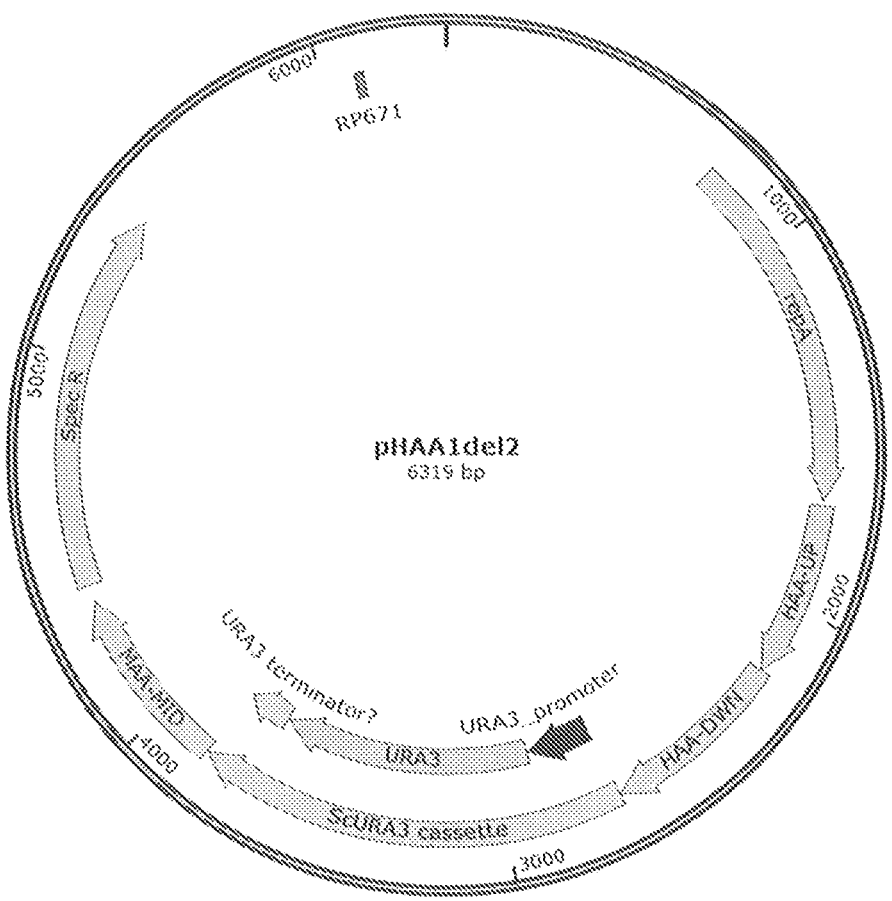
FIG. 1 Structure of pHAA1del2, a plasmid which contains the cassette used to delete S HAA1 gene from strains MYR2297 and MYR2787.

Technical terms or scientific terms used herein, have definitions as understood by those having an ordinary skill in the art, unless stated otherwise. To facilitate understanding of the invention, a description of nomenclature is provided below.

Equipment, apparatus, methods, or chemicals mentioned here means equipment, apparatus, methods or chemicals commonly operated or used by those skilled in the art, unless explicitly stated otherwise that they are equipment, apparatus, methods, or chemicals specifically used in this invention.

The use of the singular or plural nouns with the term "comprising" in the claims or in the specification refers to "one" and including "one or more", "at least one" and "one or more than one" too.

All compositions and/or methods disclosed and claims in this application aim to cover embodiments from any action, performance, modification, or adjustment without any experiment that significantly different from this invention and obtain with object with utility and resulted as same as the present embodiment according to person ordinary skilled in the art although without specifically stated in claims. Therefore, substitutable or similar object to the present embodiment, including any little modification or adjustment that clearly seen by person 3 skilled in the art should be construed as remains in spirit, scope, and concept of invention as appeared in appended claims.

Throughout this application, the term "about" is used to indicate that any value presented herein may potentially vary or deviate. Such variation or deviation may result from errors of apparatus, methods used in calculation or from individual operator implementing apparatus or methods. These include variations or deviations caused by the changes of physical properties.

In regards to nomenclature, a bacterial gene or coding region is usually named with lower case letters in italics, for example "ldhA" from E. coli, while the enzyme or protein encoded by the gene can be named with the same letters, but the first letter in upper case and without italics, for example "LdhA". A yeast gene or coding region is usually named with upper case letters in italics, for example "HAA1", while the enzyme or protein encoded by the gene can be named with the same letters, but with the first letter in upper case and without italics, for example "Haa1". For yeast strains that contain a mutation in particular gene, or have a mutant phenotype, the gene or strain is designated by lower case italicized letters, for example haa1 or Δhaa1 for a strain that lacks a functional HAA1 gene. To specify the organism from which a particular gene was derived, the gene name can be preceded by two letters indicating the genus and species. For example, the KmURA3 gene is derived from Kluyveromyces marxianus, the ScURA3 gene is derived from Saccharomyces cerevisiae.

"Yeast" means any fungal organism that is capable of growing in a single cell state under some conditions. Some yeast strains can also grow in a hyphal state or pseudohyphal (i.e., short hyphae) state under some conditions, such as under starvation.

"Lactic acid" or "D-LAC" or "D-lactic acid" means lactic acid includes its salts such as lactate "Genetic engineering" or "Genetically engineered" means an activity of introducing one or more genetic modifications into a cell or a cell produced thereby.

"Genetic modification" means an artificial alteration in a characteristic or structure of a genetic material of a cell. Genetic modifications include introducing a polynucleotide encoding a polypeptide into a cell for a substitution, addition, insertion, or deletion of one or more nucleotides with respect to a genetic material of a parent cell or a chemical modification of the genetic material of a parent cell.

"Parent cell" or "Parent" or "Parental" means an original cell or a cell having no particular genetic modification and may be used as a starting material to produce a genetically engineered cell having increased or decreased activity or production.

"Wild type" means a polypeptide or polynucleotide having no particular genetic modification "Transformant" means a cell or strain that results from installation of a desired DNA sequence, either linear or circular, and either autonomously replicating or not, into a host or parent strain.

"Mutation" means any changes from a native or parent DNA sequence, for example, an inversion, a duplication, an insertion of one or more base pairs, a deletion of one or more base pairs, a point mutation leading to a base change that creates a premature stop codon, or a missense mutation that changes the amino acid encoded at that position.

"Mutant" means a strain that comprises one or more mutations when compared to a native, wild type, parent or precursor strain.

"Cassette" means a deoxyribose nucleic acid (DNA) sequence that is capable of encoding, producing, or overproducing or alternatively, eliminating or reducing the activity of, one or more desired proteins or enzymes when installed in a host organism. A cassette for producing a protein or enzyme typically comprises at least one promoter, at least one protein coding sequence, and optionally at least one transcription terminator. A cassette can be built into a plasmid, which can be circular, or it can be a linear DNA created by polymerase chain reaction (PCR), primer extension PCR, or by in vivo or in vitro homologous recombination between ends of DNA fragments, each of which is a subset of the desired final cassette, where each subset fragment has an overlapping homology at either or both ends, designed to result in joining od adjacent fragments by homologous recombination either in vivo or in vitro. A cassette can be designed to include a selectable marker gene or DNA sequence that upon integration is surrounded by a direct repeat sequence of about 30 base pairs or more (the same sequence in the orientation present at both ends of the integrated selectable gene), such that the selectable marker can be deleted by homologous recombination between the direct repeats (also known as "looping out"), after the initial cassette containing the selectable marker has been integrated into 0.5 a chromosome or plasmid. Useful selectable marker gene include, but are not limited to, antibiotic G418 resistance (kan or kanR), hygromycin resistance (hyg or hygR), zeocin resistance (zeo or zeoR), naturicin resistance (nat or natR), and biosynthesis genes such as URA3, TRP1, TRP5, LEU2, and HIS3. For the biosynthesis genes to be used as a selectable marker, the host strain must contain a mutation in the corresponding gene, preferably a non-reverting null mutation. For example, if URA3 is used as the selectable marker gene, then the strain to be transformed must be phenotypically ura3.

"Plasmid" means a linear or circular DNA molecule that is substantially smaller that a chromosome, is separate from the chromosome of chromosomes of a microorganism, and replicates separately from the chromosome or chromosomes. A plasmid can be present in about one copy per cell or in more than one copy per cell. Maintenance of a plasmid within a microbial cell usually requires growth in a medium that selects for presence of the plasmid, for example using complementation of a chromosomal auxotrophy or an antibiotic resistance gene.

"Chromosome" or "Chromosomal" means a linear or circular DNA molecule that is substantially larger than a plasmid and usually does not require any antibiotic or nutritional selection.

"Disruption" means causing the enzyme or protein encoded by a gene or coding region to be not produced or produced in a host microorganism at a level that is less than the level found in the wild type version of the host microorganism under the same or similar growth conditions.

"Overexpression" means causing the enzyme or protein encoded by a gene or coding region to be produced in a host microorganism at a level that is higher than the level found in the wild type version of the host microorganism under the same or similar growth conditions.

"Gibson method" means a method for joining in vitro together two or more linear DNA fragments that have short (about 15-40 base pairs) overlapping homology at their ends. This method can be used to construct plasmid from synthetic linear DNA fragments, PCR fragments, or fragments generated by restriction enzymes. Kits can be purchased to perform the Gibson method, for example the NEBuilder HiFi DNA Assembly Cloning Kit (New England BioLabs, Ipswitch, Massachusetts, USA), and used as instructed by the manufacturer.

"Titer" means the concentration of a compound in a fermentation broth, usually expressed as grams per liter (g/L) or as % weight per volume (%).

To facilitate understanding of the invention, various genes are listed in Table 1.

TABLE 1

Gene names and descriptions

| Gene name | Protein or function encoded | Source microorganism |
|---|---|---|
| EcldhA | D-lactate dehydrogenase | E. coli |
| URA3 | Orotidine-5'-phosphate decarboxylase | K. marxianus |
| ScURA3 | | S. cerevisiae |
| KmURA3 | | |
| PDC1 | Pyruvate decarboxylase | K. marxianus |
| KmPDC1 | | |
| GPP1 | Glycerol-3-phosphate phosphatase | K. marxianus |
| NDE1 | NADH dehydrogenase-1 | K. marxianus |
| HAA1 | Acid-responsive transcription factor | K. marxianus |
| KmHAA1 | | |
| Kmhaa1 | | |

Unless otherwise specified, recombinant DNA and genetic engineering in this invention was carried out with methods and materials well known in the art. Plasmids and linear DNA cassettes were assembled using the "Gibson Method" according to the manufacturer's protocol, or by in vivo homologous recombination as described above.

To delete a DNA sequence or to integrate an expression cassette, the method that we generally used to assemble the cassette on a plasmid that can replicate in E. coli, or to assemble the cassette in vivo in the target yeast strain by co-transforming two or more subsections of the cassette, with adjacent subsections designed to overlap a base pairs at the ends to be joined, as well as a base pairs at the ends of the assembled cassette that are homologous with the chromosomal target sequence. All of the cassette described herein for integration in a Kluyveromyces sp. chromosome were designed to express a yeast URA3 gene (typically the ScURA3 gene or the native KmURA3 gene) and the recipient host organism has a non-reverting ura3-phenotype, typically by virtue of a deletion at the native KmURA3 locus. In order to be able to reuse URA3+ selection in subsequent engineering steps, in each cassette, the URA3 gene is surrounded by a direct repeat DNA sequences that allow deletion of the URA3 gene from the cassette after it has been integrated, by homologous recombination between said directly repeated DNA sequences, in a second step by selecting against the URA3 gene on minimal medium containing 5'-fluoroorotic acid (5'-FOA).

Therefore, the general design of disruption cassettes for integration have the following features, in the following order: 1) a sequence "Up" of a base pairs that is homologous to the target chromosomal sequence that is just upstream from the desired integration target site 2) a sequence "Down" of a base pairs that is homologous to the target chromosomal sequence that is just downstream of the desired deletion endpoint 3) a selectable marker gene such as the URA3 gene (and optionally counterselectable) 4) a sequence "Middle" of a base pairs that is homologous to at least a portion of the chromosomal target sequence that is desired to be deleted. Upon transformation and selection, the assembled cassette integrates into the chromosomal target site by homologous double recombination between the "Up" sequence and the "Middle" sequence. Transformants containing the correct integration are identified by diagnostic PCR that shows both an upstream and a downstream junction fragment of the correct expected size. In a second step the selectable marker gene is "looped out" by counterselection and homologous recombination between the "Down" sequence internal to the cassette, and the sequence that is homologous to "Down" in the chromosome that is logically present downstream from the integrated cassette.

On the other hand, the general design of an expression cassettes for integration have the following features, in the following order: 1) a sequence "Up" of a more base pairs that is homologous to the target chromosomal sequence that is just upstream from the desired integration target site 2) a sequence that is designed to be integrated, for example, a promoter-ORF-terminator combination 3) a sequence "Down" of a base pairs that is homologous to the target chromosomal sequence that is just downstream of the desired deletion endpoint 4) a selectable marker gene such as the URA3 gene (and optionally counterselectable) 5) a sequence "Middle" of a base pairs that is homologous to at least a portion of the chromosomal target sequence that is desired to be deleted. If the target chromosomal sequence is intended to be deleted without a concomitant insertion, then the second fragment 2) of the general design described above is omitted. Transformants containing the correct integration are identified by a diagnostic PCR that shows both an upstream and a downstream junction fragment of the correct expected size. In a second step the selectable marker gene is "looped out" by counterselection and homologous recombination between the "Down" sequence internal to the cassette, and the sequence that is homologous to "Down" in the chromosome that is logically present downstream from the integrated cassette.

Hereafter, invention embodiments are shown without any purpose to limit any scope of the invention.

The present invention relates to a genetically engineered *Kluyveromyces sp.* yeast cell wherein said yeast cell comprising at least a genetic modification that inactivates or deletes a nucleotide sequence encoding for an amino acid SEQ ID NO. 2.

In one embodiment, the genetically engineered *Kluyveromyces* sp. yeast cell according to the invention comprises the nucleotide sequence encoding an amino acid SEQ ID NO. 2 which is an acid responsive transcription factor Haa1.

In one embodiment, the genetically engineered *Kluyveromyces sp.* yeast cell according to the invention comprises the genetic modification that increases lactic acid tolerance as compared to the parental.

In one embodiment, the genetically engineered *Kluyveromyces sp.* yeast cell according to the invention comprises the genetic modification that increases lactic acid production as compared to the parental.

In order to confirm the disruption effect of KmHAA1 gene on lactic acid tolerance then 2 strains of *K. marxianus* were used in this invention, MYR2787 which is capable of D-LAC production and MYR2297 which is not capable of D-LAC production. *K. marxianus* MYR2787 Δhaa1 according to this invention was kept at NITE Patent Microorganisms Depositary (NPMD) in Japan under the regulations of Budapest Treaty, wherein said strain was deposited on Jun. 13, 2022 under accession number NITE BP-03669.

In another embodiment, the genetically engineered *Kluyveromyces sp.* yeast cell according to the invention can be used in all of fermentation processes for lactic acid production.

To evaluate the effect of KmHAA1 gene on lactic acid tolerance and lactic acid production, genetic modifications for disruption and overexpression of HAA1 gene were studied and also compared the results to the parental strain. The results were shown in FIG. 3-6.

The following examples are provided to further explain the invention but are not intended to limit the scope of the invention.

In order to confirm the disruption effect of KmHAA1 gene on lactic acid tolerance then 2 strains of *K. marxianus* were used in this invention, MYR2787 which is capable of D-LAC production and MYR2297 which is not capable of D-LAC production.

Method for DNA Transformation of *K. marxianus* Strain MYR2297 and MYR2787

The following chemical-based DNA transformation method was adapted from the protocol published by Abdel-Banat et al. (Abdel-Banat, 2010) to be improved for strain MYR2297 and MYR2787, many of which are named and used in the examples described herein.

A fresh single colony of the strain to be transformed was inoculated into 5 mL YPD medium consisting of, per liter, 10 g yeast extract, 20 g peptone and 3 g glucose. This starting culture was grown to saturation overnight in a shaking incubator at 30° C.

After that 5 mL of the cultivated yeast was inoculated into 45 mL YPD medium with 2% glucose at 225 rpm during a period about 4 to 8 hours in a shaking incubator at 30° C. until an OD 600 nm of about 4 to 5.

During growth of the culture, a solution of 10 mg/ml single stranded salmon sperm (ssDNA) was prepared by heating in a thermocycler for 10 minutes, and then quickly chilling the tubes in an ice-water bath. The Eppendorf tubes were prepared for each individual transformation by adding 10 µl of ssDNA solution to each of the tubes followed by 5 to 10 µl of the experimental DNA destined for transformation into the strain. Ideally, the concentration of the experimental DNA should be about 500 to 1,000 ng of DNA per plasmid.

Prepare a sterile Transformation Mixture (TM) to chemically prepare the cells for transformation that contains final concentration of PEG 3350 (40% polyethylene glycol), 2M lithium acetate (LiAc) and 1M dithiothreitol (DTT). In practice, this TM is prepared by combining three stock solutions on the day of transformation. The composition of TM per 1 mL was 800 µl of 50% PEG3350, 100 µl of 2M LiAc and 100 µl of 1M DTT.

Once the culture to be transformed reached an OD 600 nm of about 4 to 5, cells were centrifuged at 7500 rpm for 5 minutes at the room temperature. The supernatant was poured away, the cells pellet was resuspended in 1 mL of TM and centrifuged once more under the same conditions. The supernatant was removed with a micropipette and resuspended in 1 mL of TM. For subsequent steps, added 15 µl of mixed DNA and aliquot 85 µl portions of cell suspension to each of the transformation tubes and mix thoroughly about 1 to 2 minutes. Heat shock each transformation by placing the tubes in a 42° C. water baht or heating block for 1 hour.

After heat shock then pelleted and rinsed the cells in a microfuge at full speed with 1 mL of a CM minus uracil medium. Span down the cells of each transformation and pipetted away the supernatant. Resuspended each pellet with 1 mL of a fresh CM minus uracil medium and spread 100 µl of cell suspension over plate containing CM minus uracil medium. The plate was incubated at 30° C. until colonies appear, typically in 2 to 4 days.

Construction of Strain MYR2297 Harboring ΔHaa1 Disruption (MYR2297ΔHaa1)

TABLE 2

Composition of growth media. All amounts listed are per liter.
For Petri plates, 20 g/L agar was added.

| Ingredient | CM minus uracil | SDM2 | YPD |
|---|---|---|---|
| Glucose | | Variable (20-200 g) | 20 g |
| Sucrose | | Variable (20-200 g) | |
| Teknova CM-ura mix | One 1 L pack | | |
| Potassium phosphate monobasic | | | |
| Ammonium phosphate monobasic | | 13.8 g | |
| Ammonium phosphate dibasic | | 3.96 g | |
| Magnesium sulfate. 7H$_2$O | | 0.493 g | |
| Yeast extract | | | 10 g |
| Peptone | | | 20 g |
| Thiamine HCl | | 200 mcg | |
| Niacin | | 3 mg | |
| Biotin | | 10 mcg | |
| Calcium pantothenate | | 400 mcg | |
| 1000x trace elements* | | 1 ml | |
| pH (with ammonium hydroxide or phosphoric acid) | | 6.2 | |
| MES (2-(N-morpholino) ethanesulfonic acid) | | | |
| Betaine | | | |
| Sodium Chloride | | 0.234 g | |
| Potassium Chloride | | 0.521 g | |

Figure 2:
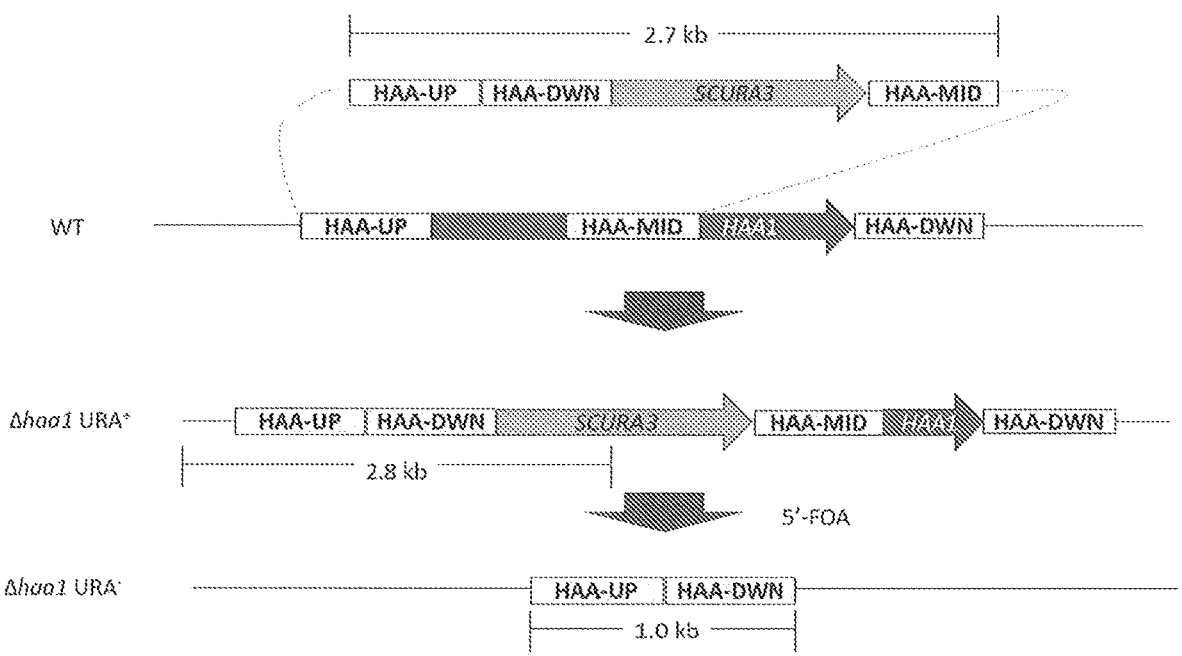
FIG. 2 Schematic diagram of the procedure used to delete HAA1 gene from strains MYR2297 and MYR2787.

*1000x Trace elements, per liter: 1.6 g FeCl$_3$•6H$_2$O, 0.1 g CuCl$_2$•2H$_2$O, 0.2 g ZnCl, 0.05 g H$_3$BO$_3$, 0.55 g MnCl$_2$•4H$_2$O, 10 ml 85% phosphoric acid The starting strain was *K. Marxianus* having an uracil auxotrophic yeast strain and a wild type HAA1 gene, namely MYR2297 HAA1. The HAA1 gene was deleted by integrating a disruption cassette constructed on plasmid pHAA1 del2. The disruption cassette comprised of 1) a "HAA Up" sequence 2) a "HAA Down" sequence 3) a ScURA3 sequence as a selectable marker and 4) a "HAA MID" sequence. A diagram showing the structure of pHAA1del2 is given in FIG. 1 and its sequence is given as SEQ ID No. 1. The procedure of KmHAA1 deletion is given in FIG. 2. The disruption cassette was designed to integrate at the target HAA1 loci, which encodes for amino acid SEQ ID No. 2, by homologous recombination. Disruptants were selected on CM minus uracil medium by selecting from the ScURA3 gene. Then, the URA3 gene was looped out by homologous recombination between direct repeats of a downstream flank on media containing 5'-FOA. The resulting single colonies were then restreaked one or more times as necessary to free the correct strain from background cells and eliminate heterozygous diploids. Correct insertions and correct loop outs were identified by PCR using appropriate primers that bracketed the borders between the ends of the cassettes and the chromosomal sequences at the target locus that are just upstream or just downstream of the integrated cassette. PCR diagnostics could not distinguish correctly integrated cassettes in haploids from correctly integrated homozygous diploids, so this distinction was not made at any step of the constructions. After the loop outs were confirmed, the native KmURA3 gene was re-installed by transformation of a linear DNA fragment obtained by PCR from *K. marxianus* wild type strain chromosomal DNA as a template to give an uracil prototroph by selection on CM minus uracil plates. The resulting strain, which now contains disruption of HAA1 gene, was named MYR2297 Δhaa1.

Construction of Strain MYR2787 Harboring Δhaa1 Disruption (MYR2787ΔHaa1)

The starting strain was *K. marxianus* having an uracil auxotrophic yeast strain and a wild type HAA1 gene that is capable of D-LAC production, namely MYR2787 HAA1. The construction of MYR2787 HAA1 are described as below. Three different cassettes designed to express the EcldhA gene were constructed on plasmids. In all three cases, the ldhA gene was expressed from the KmPDC1 promoter. The three EcldhA cassettes were designed and inserted at the target loci which were KmPDC1, KmGPP1 and KmNDE1 loci by homologous recombination. Disruptants were selected on CM minus uracil medium by selecting from the ScURA3 gene. Then the URA3 gene was looped out by homologous recombination between direct repeats of a downstream flank on media containing 5'-FOA to reuse the URA3 gene for subsequent transformations. At each transformation step and each loop out step, single colonies were restreaked one or more times as necessary to free the correct strain from background cells and to eliminate heterozygous diploids. Correct insertions and correct loop outs were identified by PCR using appropriate primers that bracketed the borders between the ends of the cassettes and the chromosomal sequences at the target locus that are just upstream or just downstream of the integrated cassette. PCR diagnostics could not distinguish correctly integrated cassettes in haploids from correctly integrated homozygous diploids, so this distinction was not made at any step of the constructions. Starting with strain MYR2297, the three/HI cassettes were installed, one at a time in the order listed above. After each initial integration of a cassette, the URA3 gene was looped out by the 5'-FOA counterselection. After the third cassette was thus installed, the native KmURA3 gene was re-installed by transformation of a linear DNA fragment obtained by a PCR from *K. marxianus* wild type strain chromosomal DNA as a template to give an uracil prototroph by selection on CM minus uracil plates. The resulting strain, which now contains three copies of the integrated ldhA gene, was named MYR2787 HAA1.

The disruption cassette of HAA1 was designed to integrate at the target loci by homologous recombination in the same procedure as described in the construction of MYR2297 Δhaa1 above. The resulting D-LAC producing strain, which now contains disruption of HAA1 gene, was named MYR2787 Δhaa1.

Construction of Yeast Strain Harboring HAA1 Overexpression (MYR2787 2X HAA1)

The HAA1 overexpression cassettes was designed to integrate into the strain MYR2787 by swapping to ldhA expression cassette. The plasmid has the following features, in the following order: 1) a strong constitutive promoter 2) a HAA1 coding region 3) a terminator 4) a ScURA3 as a selectable marker and 5) a homology to a middle sequence of ldhA locus. Although the cassette was designed to be able to integrate into any one of three ldhA expression loci, the swop integration of HAA1 overexpression cassette in GPP1 locus was selected for further examination. The resulting D-LAC producing strain, which now contains a HAA1 expression cassette at GPP 1 locus instead of ldhA expression cassette, was named MYR2787 2X HAA1.

Comparison of Yeast Growths on Lactic Acid Supplemented Medium

To determine and compare the growth performances of all yeast strains obtained as described above in low pH condition, the strains in MYR2297 HAA1, MYR2297 Δhaa1, MYR2787 HAA1, MYR2787 Δhaa1 and MYR2787 2X HAA1 were cultivated in CM minus uracil medium without and with 0.5%, 1.0%, 1.5% and 2.0% w/v of L-lactic acid. The starting pH in each media was 3.5, 2.7, 2.5, 2.4 and 2.3, respectively. All solid media contained 2% agar. Quantitative comparison of growth differences between yeast strains were done by spotting serial 10-fold dilutions, starting from $10^7$ cells, alongside each other on the same agar plates, which were incubated at 30° C. for 2 days.

Comparison of Yeast Growths and D-LAC Productions in BioLector 2 Litres

To determine and compare the yeast growth performances and its D-LAC productions, the D-LAC producing strains of MYR2787 HAA1, MYR2787 Δhaa1 and MYR2787 2X HAA1 were cultivated in flower plates in a BioLector minifermentor. Single colony of the yeast strains of MYR2787 HAA1, MYR2787 Δhaa1 and MYR2787 2X HAA1were inoculated separately into 5 mL of CM minus uracil in tube and incubated at 37° C. by using rotary incubation at speed rate 200 rpm for 12-18 hours. After that 0.1 mL of inocula were inoculated into 0.9 mL of SDM2 medium (As shown in Table 2) in BioLector cultivation plate with a starting OD 600 nm of 0.1-0.2 and pH 6.0-6.2. The flower plates were shaken and incubated respectively at speed rate 1200 rpm and 37° C. for 48 hours. The humidity was controlled at 50 80% to eliminate the water evaporation during the experiment. During the fermentation, pH was not controlled. Therefore, the pH of each cultures was falling along the fermentation due to D-LAC productions. Once the cultivation started, the biomass was automatically measured an OD 600 nm every 30 minutes. After 48 hours, the experiment was stopped. Cell mass of each strains were spin down by centrifugation. The supernatants were collected and were analyzed the amount of lactic acid content.

Figure 3:
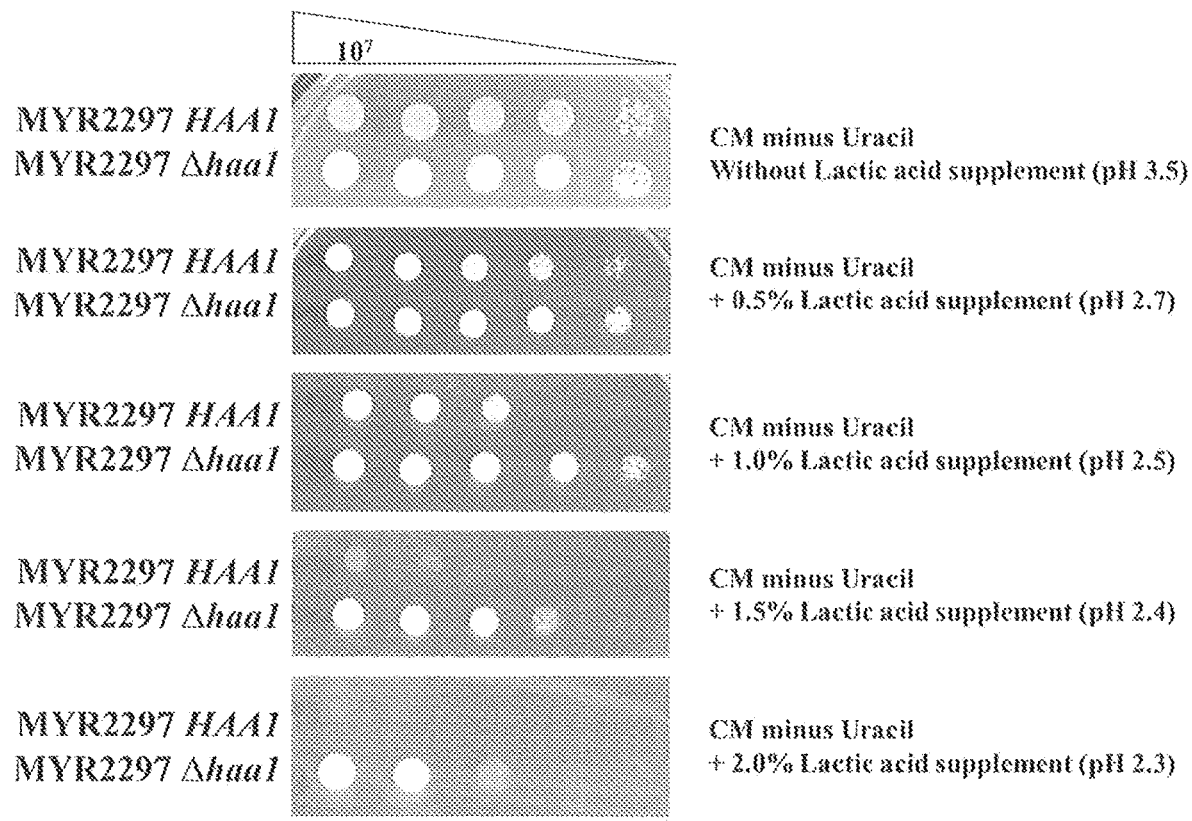
FIG. 3 Growth performance of MYR2297 parent cell (MYR2297 HAA1) and MYR2297 harboring Δhaa1 disruption (MYR2297 Δhaa1) on CM minus uracil solid medium with 0.5% (pH 2.7), 1.0% (pH 2.5), 1.5% (pH 2.4), 2.0% (pH 2.3) lactic acid supplementation or without supplementation (pH 3.5) incubated at 30° C. for 2 days.
Figure 4:
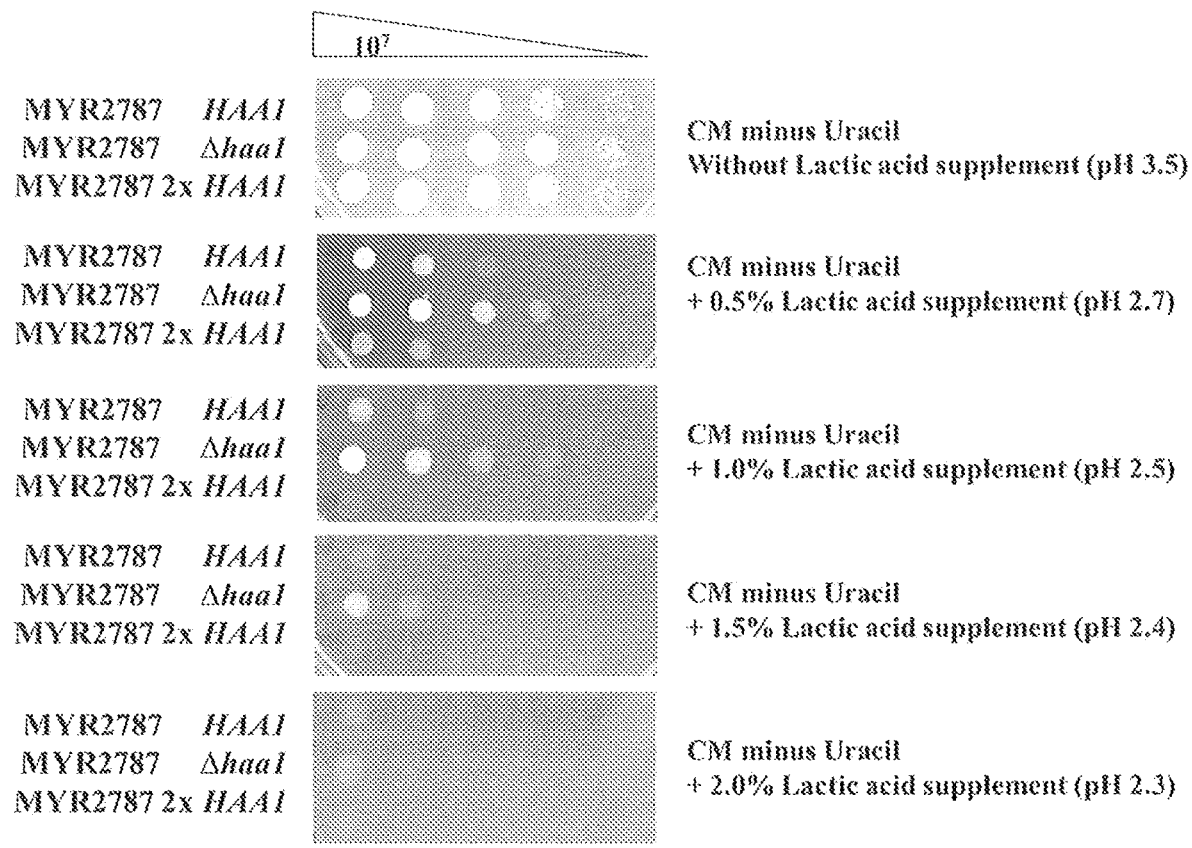
FIG. 4 Growth performance of MYR2787 parental cell (MYR2787 HAA1), MYR2787 harboring Δhaa1 disruption (MYR2787 Δhaa1) and MYR2787 harboring HAA1 overexpression (MYR2787 2X HAA1) on CM minus uracil solid medium with 0.5% (pH 2.7), 1.0% (pH 2.5), 1.5% (pH 2.4), 2.0% (pH 2.3) lactic acid supplementation or without supplementation (pH 3.5) incubated at 30° C. for 2 days.

As shown in FIGS. 3 and 4, all yeast cells having Δhaa1 disruption (MYR2297 Ahaa/and MYR2787 Δhaa1) improved its growth on low pH condition compared to the parental strains. Moreover, as shown in FIG. 4, the yeast cell having overexpression of HAA1 gene (MYR2787 2X HAA1) showed a sensitive responsivity on low pH condition compared to the parental strain. These results illustrate that yeast cells having Δhaa1 disruption increased lactic acid tolerance compared to the parental strains.

Figure 5:
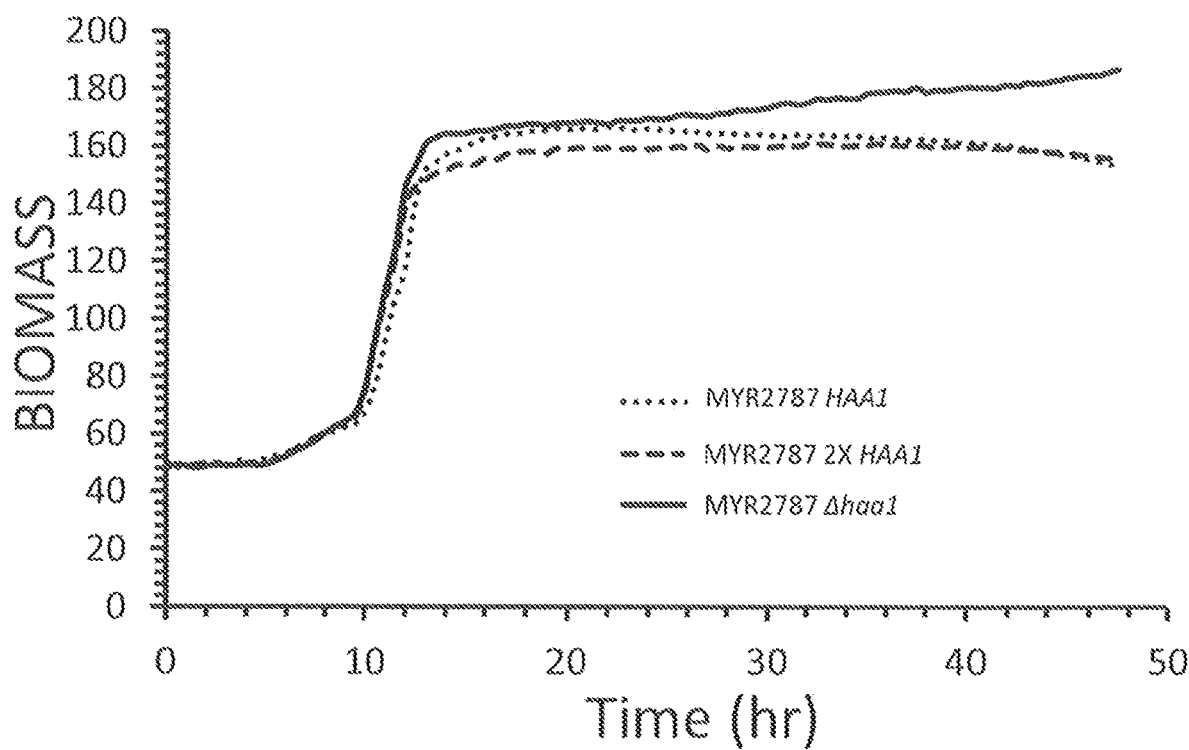
FIG. 5 Growth performances of MYR2787 parental cell (MYR2787 HAA1), MYR2787 harboring Δhaa1 disruption (MYR2787 Δhaa1) and MYR2787 harboring HAA1 overexpression (MYR2787 2X HAA1) in BioLector fermentation for 2 days.

As shown in FIG. 5, the growths of the parental strain (MYR2787 HAA1) and the yeast cell having overexpression of HAA1 gene (MYR2787 2X HAA1) stopped after 12 hours of the cultivation while the growth of the yeast cell having Δhaa1 disruption (MYR2787 Δhaa1) was continued. This indicates that the yeast cell having Δhaa1 disruption (MY R2787 Δhaa1) have improvement of growth performance in low pH condition. The results strongly confirm that yeast cell having Δhaa1 disruption increased lactic acid tolerance compared to the parental strain.

Figure 6:
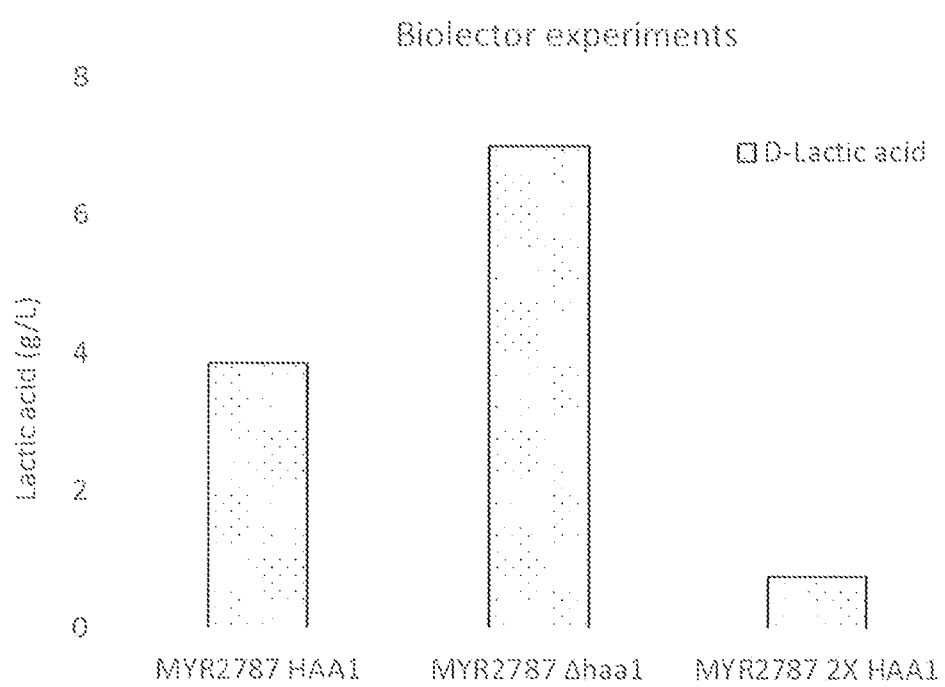
FIG. 6 D-lactic acid titers produced by MY R2787 parental cell (MYR2787 HAA1), MYR2787 harboring Δhaa1 disruption (MYR2787 Δhaa1) and MYR2787 harboring HAA1 overexpression (MYR2787 2X HAA1) in BioLector fermentation for 2 days.

As shown in FIG. 6, the D-LAC titers produced by MYR2787 parental cell (MYR2787 HAA1), MYR2787 harboring Δhaa1 disruption (MYR2787 Δhaa1) and MYR2787 harboring HAA1 overexpression (MYR2787 2X HAA1) at 48 hours were 3.8 g/L, 7.5 g/L and 0.8 g/L respectively. The results clearly demonstrate that the yeast cell having Δhaa1 disruption (MYR2787 Δhaa1) have improvement of lactic acid production without the pH control compared to the parental strain. On the other hand, the yeast cell having overexpression of HAA1 gene (MYR2787 2X HAA1) produced lactic acid less than the parental strain and the yeast cell having Δhaa1 disruption (MYR2787 Δhaa1).

From the results of all examples described above reflect that the genetically engineered yeast cell with Δhaa1 disruption which was discovered in this invention having the improvement of lactic acid tolerance, lactic acid production or a combination thereof as mentioned in the summary of the invention. This invention is the first discovery.

BEST MODE OF THE INVENTION

Best mode of the invention is as disclosed in the detailed description.

The invention claimed is:

1. A genetically engineered *Kluyveromyces marxianus* yeast cell wherein said yeast cell comprises an inactivation or a deletion of a nucleotide sequence encoding for an amino acid SEQ ID No. 2.

2. The genetically engineered *Kluyveromyces marxianus* yeast cell of claim 1, wherein said inactivation or deletion increases lactic acid tolerance as compared to the parental.

3. The genetically engineered *Kluyveromyces marxianus* yeast cell of claim 1, wherein said inactivation or deletion increases lactic acid production as compared to the parental.

4. A process for lactic acid production using said genetically engineered *Kluyveromyces marxianus* yeast cell according to claim 1, comprising the steps of:
   growing the *Kluyveromyces marxianus* yeast cell according to claim 1 in a fermentation medium to produce lactic acid; and
   optionally purifying said lactic acid from the fermentation medium.

* * * * *

SEQUENCE LISTING

```
<160> NUMBER OF SEQ ID NOS: 2

<210> SEQ ID NO 1
<211> LENGTH: 6319
<212> TYPE: DNA
<213> ORGANISM: Artificial Sequence
<220> FEATURE:
<223> OTHER INFORMATION: pHAA1del2 Plasmid

<400> SEQUENCE: 1
gttgacagta agacgggtaa gcctgttgat gataccgctg ccttactggg tgcattagcc      60
agtctgaatg acctgtcacg ggataatccg aagtggtcag actggaaaat cagagggcag     120
gaactgctga acagcaaaaa gtcagatagc accacatagc agacccgcca taaaacgccc     180
tgagaagccc gtgacgggct tttcttgtat tatgggtagt ttccttgcat gaatccataa     240
aaggcgcctg tagtgccatt tacccccatt cactgccaga gccgtgagcg cagcgaactg     300
aatgtcacga aaagacagc gactcaggtg cctgatggtc ggagacaaaa ggaatattca     360
gcgatttgcc cgagcttgcg agggtgctac ttaagccttt aggttttaa ggtctgtttt     420 gtagaggagc aaacagcgtt tgcgacatcc ttttgtaata ctgcggaact gactaaagta     480
gtgagttata cacagggctg ggatctattc tttttatctt tttttattct ttctttattc     540
tataaattat aaccacttga atataaacaa aaaaaacaca caaaggtcta gcggaattta     600
```

```
cagagggtct agcagaattt acaagttttc cagcaaaggt ctagcagaat ttacagatac    660
ccacaactca aaggaaaagg actagtaatt atcattgact agcccatctc aattggtata    720
gtgattaaaa tcacctagac caattgagat gtatgtctga attagttgtt ttcaaagcaa    780
atgaactagc gattagtcgc tatgacttaa cggagcatga aaccaagcta attttatgct    840
gtgtggcact actcaacccc acgattgaaa accctacaag gaagaacgg acggtatcgt     900 tcacttataa ccaatacgct cagatgatga acatcagtag ggaaaatgct tatggtgtat    960
tagctaaagc aaccagagag ctgatgacga gaactgtgga aatcaggaat cctttggtta   1020
aaggctttga gattttccag tggacaaact atgccaagtt ctcaagcgaa aaattagaat   1080 tagttttag tgaagagata ttgccttatc ttttccagtt aaaaaaattc ataaaatata    1140
atctggaaca tgttaagtct tttgaaaaca aatactctat gaggatttat gagtggttat   1200
taaaagaact aacacaaaag aaaactcaca aggcaaatat agagattagc cttgatgaat   1260
ttaagttcat gttaatgctt gaaaataact accatgagtt taaaaggctt aaccaatggg   1320
ttttgaaacc aataagtaaa gatttaaaca cttacagcaa tatgaaattg gtggttgata   1380
agcgaggccg cccgactgat acgttgattt tccaagttga actagataga caaatggatc   1440
tcgtaaccga acttgagaac aaccagataa aaatgaatgg tgacaaaata ccaacaacca   1500
ttacatcaga ttcctaccta cgtaacggac taagaaaaac actacacgat gctttaactg   1560
caaaaattca gctcaccagt tttgaggcaa aattttttgag tgacatgcaa agtaagcatg   1620
atctcaatgg ttcgttctca tggctcacgc aaaaacaacg aaccacacta gagaacatac   1680
tggctaaata cggaaggatc tgaggttctt atggccatta gccatcatcg tatccgatat   1740
tcaagtatca tcacacttac caacacaatt attttttttt tttttatttt taaatattaa   1800
gaaaagagag aataaagaag aagtggtaaa agacaaacaa ggagcaagcg tttagtgggg   1860
atctaacaaa caacacaaca acaacatact ctgtgctttg aagtgtaaac tactatatca   1920
ttatcattaa ttttttggata ttggattttg gtttttttt tctgtcgaga acctctcatt   1980
acttgggctt taatttaaag tcataaaatta ttcgttttat ttcatttcat ttcattttat   2040
tttattttaa tattgggaaa tttactctct caatagtgtg tgcttttaaa aaccgggttc   2100
caaaataggt tttagcgcac agatacgggt tctggggaaa caccagcagc agcagtagcg   2160
aaagttttcc accgtctcca gccttcttcc tggtcatttt tttcgataca agccaactta   2220
ataacaaata tatatatgtg ttatctattt ctacctaatt aaatcggtac aatccgttat   2280
tgaatgtaat agttctaatt atatttgtta gcacgtcttt cattttttcc cccaaatgct   2340
ctatatatat tcttactctc gctactatat tttatataat aagagactaa tcgataatat   2400
caaattttaa attatacttg ttgttaccca tctatataca ctgaaccctc tccgagagca   2460
cataggtgta tgacaatccg gtatcaaacc attcaatggg agatatactg gaaaacaaaa   2520
cttatatctt tgtagttgtg ctcattcttt agtagatggt cattggtttt tgccaatgca   2580
ctgtgatcca aatggttcca cgaggtagca tcaccataca acattacagg cgcttttatc   2640
atttgtttac catttttgca acgcttacag ttgtatgtct cgttcaattc atcattttt    2700 ttttattctt ttttttgatt tcggtttctt tgaaattttt tgattcggt aatctccgaa    2760 cagaaggaag aacgaaggaa ggagcacaga cttagattgg tatatatacg catatgtagt   2820
gttgaagaaa catgaaattg cccagtattc ttaacccaac tgcacagaac aaaaacctgc   2880
aggaaacgaa gataaatcat gtcgaaagct acatataagg aacgtgctgc tactcatcct   2940
```

```
agtcctgttg ctgccaagct atttaatatc atgcacgaaa agcaaacaaa cttgtgtgct   3000
tcattggatg ttcgtaccac caaggaatta ctggagttag ttgaagcatt aggtcccaaa   3060
atttgtttac taaaaacaca tgtggatatc ttgactgatt tttccatgga gggcacagtt   3120
aagccgctaa aggcattatc cgccaagtac aattttttac tcttcgaaga cagaaaattt   3180
gctgacattg gtaatacagt caaattgcag tactctgcgg gtgtatacag aatagcagaa   3240
tgggcagaca ttacgaatgc acacggtgtg gtgggcccag gtattgttag cggtttgaag   3300
caggcggcag aagaagtaac aaaggaacct agaggccttt tgatgttagc agaattgtca   3360
tgcaagggct ccctatctac tggagaatat actaagggta ctgttgacat tgcgaagagc   3420
gacaaagatt ttgttatcgg ctttattgct caaagagaca tgggtggaag agatgaaggt   3480
tacgattggt tgattatgac acccggtgtg ggtttagatg acaagggaga cgcattgggt   3540
caacagtata gaaccgtgga tgatgtggtc tctacaggat ctgacattat tattgttgga   3600
agaggactat ttgcaaaggg aagggatgct aaggtagagg gtgaacgtta cagaaaagca   3660
ggctgggaag catatttgag aagatgcggc cagcaaaaact aaaaaactgt attataagta   3720
aatgcatgta tactaaactc acaaattaga gcttcaattt aattatatca gttattaccc   3780
gggaatctcg gtcgtaatga tttttataat gacgaaaaaa aaaaaattgg aaagaaaaag   3840
cttggacaca gtaaaaaaca cagtcgggct tgaaccgcta agtataatga aacccatcac   3900
tccaaatact agaacaaagg ttggtgaagt ctatatccca ctaacagagt acgtcccaac   3960
aagtataacg tcttctcacg accaaacaga cagcatcaac ccacttctca tgggcgacag   4020
cctgtccata tatgacgatg gccagtctga tactcctaat gtaacatact tcgctgatac   4080
ttctaaaagt atgtcgtata cccagttgaa ggaacagcgg aagtctgtca acaatgaaca   4140
cgttccttca caaagagtgc ctctagccaa cactggtcgc tcctcttcct ttatctctaa   4200
tatatcatct catgactccg taatctcgaa taacgatttc ataagttcga tgaacagttc   4260
ggattctctt tcgtcgatgc tgcaaggtgg taacgctcac cattaccagg atatgctcca   4320
tcaccccagc aatggcagag gcatggacat aagcctgttc ggttcgtaag ctgtaatgca   4380
agtagcgtat gcgctcacgc aactggtcca gaaccttgac cgaacgcagc ggtggtaacg   4440
gcgcagtggc ggttttcatg gcttgttatg actgttttt tggggtacag tctatgcctc   4500
gggcatccaa gcagcaagcg cgttacgccg tgggtcgatg tttgatgtta tggagcagca   4560
acgatgttac gcagcagggc agtcgcccta aaacaaagtt aaacatcatg agggaagcgg   4620
tgatcgccga agtatcgact caactatcag aggtagttgg cgtcatcgag cgccatctcg   4680
aaccgacgtt gctggccgta catttgtacg gctccgcagt ggatggcggc ctgaagccac   4740
acagtgatat tgatttgctg gttacggtga ccgtaaggct tgatgaaaca acgcggcgag   4800
ctttgatcaa cgacctttg gaaacttcgg cttcccctgg agagagcgag attctccgcg   4860
ctgtagaagt caccattgtt gtgcacgacg acatcattcc gtggcgttat ccagctaagc   4920
gcgaactgca atttggagaa tggcagcgca atgacattct tgcaggtatc ttcgagccag   4980
ccacgatcga cattgatctg gctatcttgc tgacaaaagc aagagaacat agcgttgcct   5040
tggtaggtcc agcggcggag gaactctttg atccggttcc tgaacaggat ctatttgagg   5100
cgctaaatga aaccttaacg ctatggaact cgccgcccga ctgggctggc gatgagcgaa   5160
atgtagtgct tacgttgtcc cgcatttggt acagcgcagt aaccggcaaa atcgcgccga   5220
aggatgtcgc tgccgactgg gcaatggagc gcctgccggc ccagtatcag cccgtcatac   5280
ttgaagctag acaggcttat cttggacaag aagaagatcg cttggcctcg cgcgcagatc   5340
```

-continued

```
agttggaaga atttgtccac tacgtgaaag gcgagatcac caaggtagtc ggcaaataat    5400
gtctaacaat tcgttcaagc cgacgccgct tcgcggcgcg gcttaactca agcgttagat    5460
gcactaagca cataattgct cacagccaaa ctatcaggtc aagtctgctt ttattatttt    5520
taagcgtgca taataagccc tacacaaatt gggagatata tcatgaaagg ctggcttttt    5580
cttgttatcg caatagttgg cgaagtaatc gcaacatccg cattaaaatc tagcgagggc    5640
tttactaagc tgatccggtg gatgaccttt tgaatgacct ttaatagatt atattactaa    5700
ttaattgggg accctagagg tccccttttt tattttaaaa attttttcac aaaacggttt    5760
acaagcatac gttggccgat tcattaatgc agctggcacg acaggtttcc cgactggaaa    5820
gcgggcagtg agcgcaacgc aattaatgtg agttagctca ctcattaggc accccaggct    5880
ttacacttta tgcttccggc tcgtatgttg tgtggaattg tgagcggata caatttcac     5940
acaggaaaca gctatgacca tgattacgcc aagcttgcat gcctgcaggt cgactctaga    6000
ggatccccgg gtaccgagct cgaattcact ggccgtcgtt ttacaacgtc gtgactggga    6060
aaaccctggc gttacccaac ttaatcgcct tgcagcacat ccccctttcg ccagctggcg    6120
taatagcgaa gaggcccgca ccgatcgccc ttcccaacag ttgcgcagcc tgaatggcga    6180
atggcgcctg atgcggtatt ttctccttac gcatctgtgc ggtatttcac accgcatatg    6240
gtgcactctc agtacaatct gctctgatgc cgcatagtta agccagcccc gacacccgcc    6300
aacaccgct gacgaattc                                                  6319
```

<210> SEQ ID NO 2
<211> LENGTH: 599
<212> TYPE: PRT
<213> ORGANISM: Kluyveromyces marxianus

<400> SEQUENCE: 2

```
Met Val Leu Ile Asn Gly Val Lys Tyr Ala Cys Glu Arg Cys Ile Arg
1               5                   10                  15

Gly His Arg Val Thr Thr Cys Asn His Thr Asp Gln Pro Leu Thr Met
            20                  25                  30

Ile Lys Pro Lys Gly Arg Pro Ser Thr Thr Cys Ala His Cys Lys Glu
        35                  40                  45

Leu Arg Lys Ser Lys Asn Ala Asn Pro Ser Gly Gln Cys Thr Cys Gly
    50                  55                  60

Arg Gln Asp Lys Lys Arg Leu Ala Gln Lys Val Lys Glu Glu Ala Ser
65                  70                  75                  80

Cys Thr Cys Lys Thr Asp Pro Asp His Cys Ala Cys His Lys Lys Arg
                85                  90                  95

Gly Ala Lys Arg Lys Thr Lys Gly Gln Asn Ser Gly Thr Ser Ile Gly
            100                 105                 110

Leu Asp Leu Asp Gly Lys Val Ser Lys Ser Asn Gly Tyr Ser Phe Gln
        115                 120                 125

Ser Leu Pro Ser Ile Asn Ser Ser Gln Ser Leu Asp Lys Asp Ile Ser
    130                 135                 140

Asn Leu Leu Gly Ser Pro Ile Ser Met Asn Thr Ser Phe Ser Thr Gly
145                 150                 155                 160

Trp Asp Thr Gly Ser Ile Ser Ser Ser Asn Arg Ser Pro Pro Gly Ser
                165                 170                 175

Gly Asn Thr Tyr Ser Asn Ile Ser Asn Gly Asn Thr Gly Thr Ile Ser
            180                 185                 190
```

-continued

```
Asn Asn Asn Asn Asn Asn Asn His His His His Lys His
        195                 200             205

Gly Gln Asp Thr Ser Lys Asn Thr Val Gly Leu Glu Pro Leu Ser Ile
    210                 215                 220

Met Lys Pro Ile Thr Pro Asn Thr Arg Thr Lys Val Gly Glu Val Tyr
225                 230                 235                 240

Ile Pro Leu Thr Glu Tyr Val Pro Thr Ser Ile Thr Ser Ser His Asp
                245                 250                 255

Gln Thr Asp Ser Ile Asn Pro Leu Leu Met Gly Asp Ser Leu Ser Ile
            260                 265                 270

Tyr Asp Asp Gly Gln Ser Asp Thr Pro Asn Val Thr Tyr Phe Ala Asp
        275                 280                 285

Thr Ser Lys Ser Met Ser Tyr Thr Gln Leu Lys Glu Gln Arg Lys Ser
    290                 295                 300

Val Asn Asn Glu His Val Pro Ser Gln Arg Val Pro Leu Ala Asn Thr
305                 310                 315                 320

Gly Arg Ser Ser Ser Phe Ile Ser Asn Ile Ser Ser His Asp Ser Val
                325                 330                 335

Ile Ser Asn Asn Asp Phe Ile Ser Ser Met Asn Ser Ser Asp Ser Leu
            340                 345                 350

Ser Ser Met Leu Gln Gly Gly Asn Ala His His Tyr Gln Asp Met Leu
    355                 360                 365

His His Pro Ser Asn Gly Arg Gly Ser Gly Phe Asn Pro Val His Ile
        370                 375                 380

Glu Gln Ser Pro Asn Val Tyr Gly Phe Asp Thr Asp Ser Val Arg Ser
385                 390                 395                 400

Val Glu Val Leu Ser Ile Thr Pro Ser Phe Met Asp Ile Pro Glu Ser
                405                 410                 415

Lys Gln Ala Ser Ala Glu Ser Asn Thr Ser Ser Ser Gly Tyr Ile Ser
            420                 425                 430

Trp Lys Gly Val Asn Ser Arg Arg Glu Arg Ser Val Ser Ile His Lys
    435                 440                 445

Asn His Arg Tyr Asp Ser Glu Asn Lys Arg Lys Arg His Pro Leu Thr
        450                 455                 460

Ser Ala Asn Ser Ser Lys Gln Gln Ile Lys Ser Met Ile Leu Pro Ile
465                 470                 475                 480

Glu Glu Asn Asn Asn His Asn Ser Ser Ser Asn Glu Asn Thr Ala
                485                 490                 495

Ala Thr Leu Pro Thr Thr Ser Asn Asn Phe Asn Ser Pro Ala Asp Ser
            500                 505                 510

Thr Asn Thr Ala Leu Ser Ser Lys Ala Ala Phe Gly Asp Gln Ser Val
    515                 520                 525

Phe Ser Thr Glu Arg Arg Gly Leu Glu Pro Ser Phe Val Asp Pro Gln
    530                 535                 540

Phe Ser Pro Asp Phe Asn Pro Ser Leu Lys Gln Ser His Met Ile Asn
545                 550                 555                 560

Gln Asn Ile Ile Asp Asn Asn Ser Leu Phe Ser Gly Thr Ser Glu Gly
                565                 570                 575

Asn Asn Pro Ser Pro Asn Asp Ile Phe Pro Val Glu Phe Ala Asp Ile
            580                 585                 590

Asp Asp Leu Met Thr His Leu
        595
```